(12) United States Patent
Morgan

(10) Patent No.: US 9,346,836 B2
(45) Date of Patent: *May 24, 2016

(54) SALTS OF ISOPHOSPHORAMIDE MUSTARD AND ANALOGS THEREOF AS ANTI-TUMOR AGENTS

(71) Applicant: ZIOPHARM Oncology, Inc., Boston, MA (US)

(72) Inventor: Lee R. Morgan, New Orleans, LA (US)

(73) Assignee: ZIOPHARM Oncology, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/328,125

(22) Filed: Jul. 10, 2014

(65) Prior Publication Data

US 2015/0152125 A1    Jun. 4, 2015

Related U.S. Application Data

(63) Continuation of application No. 13/541,522, filed on Jul. 3, 2012, now Pat. No. 8,795,659, which is a continuation of application No. 11/666,215, filed as application No. PCT/US2005/038523 on Oct. 25, 2005, now Pat. No. 8,232,262.

(60) Provisional application No. 60/672,707, filed on Apr. 18, 2005, provisional application No. 60/622,087, filed on Oct. 25, 2004.

(51) Int. Cl.
| | | |
|---|---|---|
| *A61K 31/664* | (2006.01) | |
| *A61K 45/06* | (2006.01) | |
| *C07C 229/26* | (2006.01) | |
| *C07F 9/22* | (2006.01) | |

(52) U.S. Cl.
CPC ............ *C07F 9/222* (2013.01); *A61K 31/664* (2013.01); *A61K 45/06* (2013.01); *C07C 229/26* (2013.01)

(58) Field of Classification Search
CPC ...................................... C07F 9/222
USPC .................. 514/385, 89, 94; 546/22; 548/385
See application file for complete search history.

(56) References Cited

U.S. PATENT DOCUMENTS

| | | | |
|---|---|---|---|
| 5,055,459 A | 10/1991 | Andersson et al. | |
| 5,468,499 A | 11/1995 | Chan et al. | |
| 5,530,020 A | 6/1996 | Gunawardana et al. | |
| 5,912,264 A | 6/1999 | Wittman et al. | |
| 6,197,760 B1 | 3/2001 | Struck | |
| 6,610,860 B2 | 8/2003 | Holton | |
| 7,678,778 B2* | 3/2010 | Morgan ........................... | 514/89 |
| 2008/0255056 A1 | 10/2008 | Amedio et al. | |

FOREIGN PATENT DOCUMENTS

| | | |
|---|---|---|
| JP | 51-059886 A | 5/1976 |
| WO | WO-00/71134 A1 | 11/2000 |
| WO | WO-01/79158 A2 | 10/2001 |
| WO | WO-02051398 A1 | 7/2002 |
| WO | WO-2004018478 A2 | 3/2004 |
| WO | WO-2006/047575 | 5/2006 |

OTHER PUBLICATIONS

Boal et al., "Phosphorus-31 NMR Studies of the Kinetics of Bisalkylation by Isophosphoramide Mustard: Comparisons with Phosphoramide Mustard," J. Med. Chem., 32(8):1768-1773 (1989).
Chamberlain, M.C. et al., "Treatment of Leptomeningeal Metastasis With Intraventricular Administration of Depot Cytarabine (DTC 101): A Phase I Study," Arch. Neurology, vol. 50, No. 3, pp. 261-264 (Mar. 1993)—6 pages.
Chemical Abstracts Accession No. 81:37378 & SU 427945 A1 (Institute of Heteroorganic Compounds) May 15, 1994.
Cole et al., "Gas chromatography-electron ionization mass spectrometry and liquid chromatography—electrospray tandem mass spectrometry fordetermination of impurities in the anti-cancer drug isophosphoramide mustard," International Journal of Mass Spectrometry, 231:147-155 (2004).
Database Beilstein [online], Beilstein Institute for Organic Chemistry, Frankfurt-Main, DE, XP002368999, Database accession No. BRN 2249643, abstract, and Breil, S. et al.: Phosphorus, Sulfur Silicon Relat. Elem., 177(8-9):1939-1940 (2002).
Database Beilstein [online], Beilstein Institute for Organic Chemistry, Frankfurt-Main, DE, XP002453066, Database accession No. BRN 6845680, abstract, Shulman-Roskes et al.: J. Labelled Comp. Radiopharm., 34(3):231-238 (1994).
Database Beilstein [online], Beilstein Institute for Organic Chemistry, Frankfurt-Main, DE, XP002453067 retrieved from XFIRE, Database accession No. BRN7291472, abstract.

(Continued)

*Primary Examiner* — James O Wilson
*Assistant Examiner* — Ebenezer O Sackey
(74) *Attorney, Agent, or Firm* — Wilmer Cutler Pickering Hale and Dorr LLP

(57) ABSTRACT

The present disclosure relates to salts and compositions of isophosphoramide mustard and isophosphoramide mustard analogs. In one embodiment the salts can be represented by the formula I: (I) wherein $A^+$ represents an ammonium species selected from the protonated (conjugate acid) or quaternary forms of aliphatic amines and aromatic amines, including basic amino acids, heterocyclic amines, substituted and unsubstituted pyridines, guanidines and amidines; and X and Y independently represent leaving groups. Also disclosed herein are methods for making such compounds and formulating pharmaceutical compositions thereof. Methods for administering the disclosed compounds to subjects, particularly to treat hyper-proliferative disorders, also are disclosed.

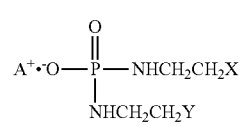

(I)

49 Claims, 4 Drawing Sheets

(56) References Cited

OTHER PUBLICATIONS

Database Beilstein [online], Beilstein Institute for Organic Chemistry, Frankfurt-Main, DE, XP002453069, retrieved from XFIRE, Database accession No. BRN 6559377, BRN 6509713, BRN 6503975, abstract.
Database Beilstein [online], Beilstein Institute for Organic Chemistry, Frankfurt-Main, DE, XP002453070 retrieved from XFIRE, Database accession No. 9763485, abstract, Misiura, K.: Pharmazie, 59(9):668-672 (2004).
Database Beilstein [online], Beilstein Institute for Organic Chemistry, Frankfurt-Main, DE, XP002453071 retrieved from XFIRE, Database accession No. BRN 9261194, BRN 9259456, abstract, Rouvese et al.: Phosphorus, Sulfur, Silicon Rel. Elem.,177(6-7):1735-1738 (2002).
Database Beilstein [online], Beilstein Institute for Organic Chemistry, Frankfurt-Main, DE, XP002453072 retrieved from XFIRE, Database accession No. BRN 8468593, BRN 8458718, abstract, Dirven et al.: Chem. Res. Txicol., 8(7):979-986 (1995).
Database Beilstein [online], Beilstein Institute for Organic Chemistry, Frankfurt-Main, DE; XP002369000, Database accession No. BRN 6835849 abstract, and Shulman-Roskes et al.: J. Labelled Comp. Radiopharm., 34(3):231-238 (1994).
Database Biosis [online], Biosciences Information Service, Philadelphia, PA, US (1994), Shulman-Roskes Ellen M. et al., "Synthesis of 15N labeled isophosphoramide mustard," XP002369092, Database accession No. PREV199497274456 abstract and Journal ofLabelled Compounds and Radiopharmaceuticals, 34(3)231-237 (1994).
Database CA [online] Chemical Abstracts Service, Columbus, OH, US; Millis et al., "Comparison of the Protonation of Isophosphoramide Mustard and Phosphoramide Mustard," XP002453068, retrieved from STN Database accession No. 1995:592274, abstract.
European Examination Report for European Patent Application No. 10178422.1 mailed Jul. 3, 2013. 6 pages.
European Search Report and Written Opinion dated Dec. 14, 2011 for corresponding European Patent Application No. 10178422.1 (7 pages).
European Search Report and Written Opinion dated Dec. 2, 2011 for corresponding European Patent Application No. 10178414.8 (7 pages).
Fries, K.M. et al. "$^{31}$P NMR and Chloride Ion Kinetics of Alkylating Monoester Phosphoramidates," J. Med. Chem. 1991, 34, 565-569.
Germann et al., "Comparative preclinical toxicology and pharmacology of isophosphoramide mustard, the active metabolite of ifosfamide," Cancer Chemotherapy and Pharmacology, Springer-Verlag Heidelberg, 55:143-151 (2005). Epub 2004.
Han, S.Y., et al., "Synthesis of $^{17}$O (and $^{18}$O) Labelled Isophosphoramide Mustard" Journal of Labelled Compounds and Radiopharmaceuticals 34:(3):247-254 (1994).
Howell, S.B., "Clinical applications of a novel sustained-release injectable drug delivery system: DepoFoam™ technology," The Cancer Journal, vol. 7, No. 3, pp. 219-227 (May/Jun. 2001)—10 pages.
Katre, N.V. et al., "Multivesicular Liposome (DepoFoam) Technology for the Sustained Delivery of Insulin-like Growth Factor-I (IGF-I)," Journal of Pharmaceutical Sciences, vol. 87, No. 11, pp. 1341-1346 (Nov. 1998)—6 pages.
Ludeman et al., "Synthesis and Antitumor Activity of Cyclophosphamide Analogues. 4. Preparation, Kinetic Studies, and Anticancer Screening of 'Phenylketophosphamide' and Similar Compounds Related to the Cyclophosphamide Metabolite Aldophosphamide," J. Med. Chem., 29(5):716-727 (1986).
Millis et al., "Comparison of the Protonation of Isophosphoramide Mustard and Phosphoramide Mustard," J. Med. Chem., 38(12):2166-2175 (1995).
Misiura, K. et al., Isophosphoramide mustard analogues as prodrugs for anti-cancer gene-directed enzyme-prodrug therapy (GDEPI) Acta Biochimica Polonica 49(1):169-176 (2002).
Pohl et al., Cancer Chemotherapy and Pharmacology, vol. 35.
Rauen et al., "Alkylans-Alkylandum-Reaktionen 2-Chloraethylmin Und Phosphamidverbindungen Als Alkylantien," Arzneimittel Forschung. Drug Research, ECV Editio Cantor Verlag, Aulendorf, DE, 21(4):518-524 (1971) XP001105865.
Spears, C.P. "Nucleophilic Selectivity Ratios of Model and Clinical Alkylating Agents by 4-(4'-Nitrobenzyl)pyridine Competition," Molecular Pharmacology, 19:496-504, Received Aug. 13, 1980; Accepted 3, 1980.
Springer et al., "Isoposphoramide Mustard and Its Mechanism of Bisalkylation," J. Org. Chem., 63(21):7218-7222 (1998).
Struck et al., "Isophosphoramide mustard, a metabolite of ifosfamide with activity against murine tumours comparable to cyclophosphamide," Br. J. Cancer, 47:015-026 (1983).
Voelcker, G., et al., "Structure/activity studies with thiazolidinyl-and perhydrothiazinyl-phosphamide esters," Journal of Cancer Research and Clinical Oncology, vol. 124(6):197-300 (1998).
Wagner, John, Intrasubject Variation in Elimination Half-lives of Drugs Which Are Appreciated Metabolized, Journal of Pharmacokinetics and Biopharmaceutics, vol. 1, No. 2, 1973.
Ye, Q. et al., "DepoFoam™ technology: a vehicle for controlled delivery of protein and peptide drugs," Journal of Controlled Release, vol. 64, Issues 1-3, pp. 155-166 (Feb. 2000)—12 pages.
Zakharov, S. et al. "Catalytic phosphorylation of polyfluoroalkanols. Communication 5. Catalytic phosphorylation of a α-polyfluoroalkylbenzyl alcohols with phosphoryl chloride," Bulletin of the Academy of Sciences of the USSR 25(8):1727-31 (1976).
Zheng et al., "Preclinical pharmacokinetics and stability of isophosphoramide mustard," Cancer Chemother Pharmacol, 33:391-398 (1994).

\* cited by examiner

SALTS OF ISOPHOSPHORAMIDE MUSTARD AND ANALOGS THEREOF AS ANTI-TUMOR AGENTS

CROSS REFERENCE TO RELATED APPLICATIONS

This application is a continuation of U.S. patent application Ser. No. 13/541,522, filed Jul. 3, 2012, which is a continuation of U.S. patent application Ser. No. 11/666,215, filed Mar. 27, 2008, now U.S. Pat. No. 8,232,262, which is a national stage under 35 U.S.C. §371 of International Patent Application No. PCT/US2005/038523, filed Oct. 25, 2005, which claims priority to U.S. Provisional Patent Application No. 60/672,707, filed on Apr. 18, 2005 and U.S. Provisional Patent Application No. 60/622,087, filed Oct. 25, 2004, the entire contents of which are hereby incorporated by reference.

STATEMENT OF GOVERNMENT RIGHTS

This invention was made with government support under Grant No. 5R44CA083552-03 awarded by the National Cancer Institute. The government has certain rights in the invention.

FIELD

This disclosure concerns salts of isophosphoramide mustard and analogs thereof. Also disclosed are pharmaceutical compositions and methods for using such compositions to treat hyper-proliferative disorders.

BACKGROUND

Autopsies of soldiers killed by mustard gas in World War I indicated that sulfur mustard has a disproportionate effect on rapidly dividing cells and suggested that sulfur mustard compounds might have antitumor effects. Indeed, early researchers attempted to treat cancer by direct injection of sulfur mustard into tumors. This research was limited by the extreme toxicity of sulfur mustard compounds and nitrogen mustard analogs, such as mechlorethamine, were investigated as less toxic alternatives.

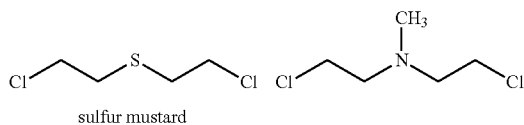

sulfur mustard

In general mustard compounds exert their cytotoxic effects by alkylating DNA, such as at the N-7 position of a guanine residue. The mechanism of alkylation by mustard compounds is illustrated in Scheme 1. With reference to Scheme 1, mustard compounds have an internal nucleophile that assists in chloride displacement, by as shown for the case of mechlorethamine, forming an aziridinium intermediate. Because mechlorethamine has two leaving groups, the nucleophilic substitution mechanism depicted in Scheme 1 can be repeated resulting in a DNA or protein-DNA crosslink.

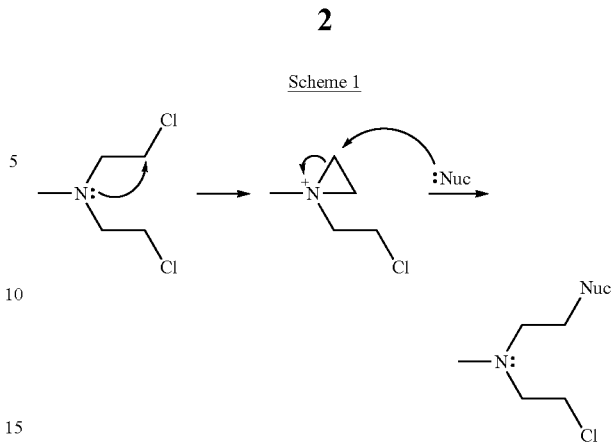

Scheme 1

Mechlorethamine is extremely reactive and as a result is non-selective. Thousands of alkylating agents have been designed and prepared using mechlorethamine as a model. However, few of these compounds have demonstrated sufficient therapeutic superiority to mechlorethamine to warrant clinical trials.

Because of the lack of selectivity of most methchlorethamine analogs, prodrugs, such as phosphoramide compounds, which can be activated by the high concentration of phosphoramidases present in neoplastic cells, have been investigated. Two phophoramide alkylating agents, cyclophosphamide (CPA) and the isomeric compound Ifosfamide (Ifos) have proved to be particularly effective.

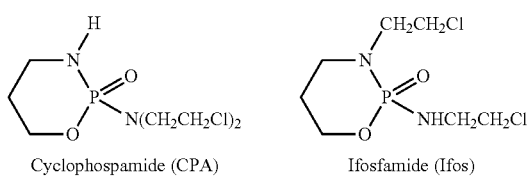

Cyclophospamide (CPA)   Ifosfamide (Ifos)

The metabolic pathway of CPA is similar to that of Ifos (the metabolism of Ifos is illustrated in FIG. 1) and thus the two compounds share common drawbacks. Perhaps most important is their dose limiting toxicity due to hemorrhagic cystitis. The hemorrhagic cystitis is believed to be induced by the production of acrolein during the activation of both CPA and Ifos. Acrolein is an active electrophile that reacts with thiols under physiological conditions, which may be responsible for its liver toxicity in the form of glutathione depletion. Finally, acrolein has been demonstrated to be a teratogen and a potent mutagen, and this may be responsible for the link between CPA treatment and serious side effects, such as bladder carcinoma and other malignancies.

With reference to FIG. 1, isophosphoramide mustard (IPM) is a common metabolite of CPA and Ifos. IPM is thought to be responsible for at least a portion of the antitumor activity exhibited by CPA and Ifos. Efforts to use IPM as an anticancer agent directly have been unsuccessful due in part to the compound's instability. IPM has been synthesized and preliminary biological evaluations of the compound have been conducted, but unfortunately IPM is rod unstable to be isolated and used for human treatment.

SUMMARY OF THE DISCLOSURE

Disclosed herein are compounds of the formula

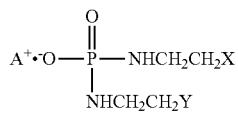

wherein A⁺ represents an ammonium species selected from the protonated (conjugate acid) or quaternary forms of aliphatic amines and aromatic amines, including basic amino acids, heterocyclic amines, substituted and unsubstituted pyridines, guanidines and amidines; and X and Y independently represent leaving groups.

In one embodiment, pharmaceutical compositions are disclosed that include one or more of the compounds described above. In one aspect of this embodiment, the compositions can include one or more therapeutic agents other than those described by the formula above for use in combination therapy.

In another embodiment, methods for treating mammalian subjects, such as human subjects, having hyperproliferative disorders are disclosed. Such methods can employ one or more of the compounds and compositions described above.

In another aspect, disclosed herein are sterile pharmaceutical compositions of compounds of the formula

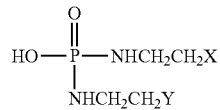

wherein X and Y independently represent leaving groups, or a pharmaceutically acceptable salt thereof. Methods of preparing such compositions, including rendering the composition sterile by using a sterile antimicrobial filter, are also described. In certain embodiments, such filtration may be performed with less than 10% decomposition of the active ingredient, preferably less than 5%, 2%, or even less than 1% decomposition.

Also disclosed herein is a method for producing a lyophilisate comprising a compound of the formula above. In one embodiment the method comprises contacting isophosphoramide mustard or an analog thereof with an amine base in the presence of water and lyophilizing the resulting mixture.

DETAILED DESCRIPTION

Figure 1:
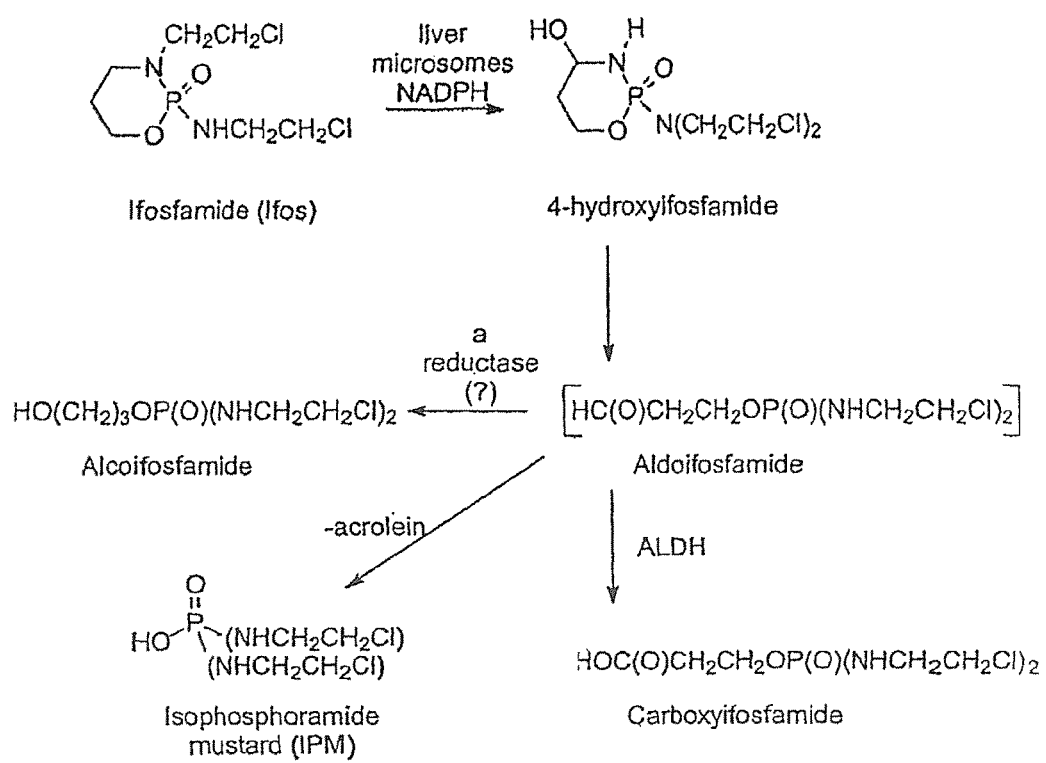
FIG. 1 is a scheme illustrating the metabolism of ifosfamide including the production of acrolein and isophosphoramide mustard.

The following explanations of terms and examples are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be understood to have the following meanings:

"Optional" or "optionally" means that the subsequently described event or circumstance can but need not occur, and that the description includes instances where said event or circumstance occurs and instances where it does not.

The term "amino acid" refers to both natural and unnatural amino acids, including α-amino acids, in their D and L stereoisomers for chiral amino acids. Examples of basic amino acid residues include those having a basic side chain, such as an amino or guanidino group. Basic amino acid residues include, without limitation, arginine, histidine, homoarginine, lysine, homolysine and ornithine.

The term "antibody" means an immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. These proteins may be derived from natural sources, or partly or wholly synthetically produced. Antibodies used herein may be monoclonal or polyclonal.

As used herein, "aliphatic amine" refers to a compound of the formula NR$^1$R$^2$R$^3$, wherein at least one of R$^{1\text{-}3}$ is an aliphatic group.

The term "acyclic aliphatic amine" refers to an aliphatic amine as above, wherein at least one of the aliphatic groups is acyclic.

The term "heterocyclic amine" refers to a compound of the formula NR$^1$R$^2$R$^3$, wherein at least one of R$^{1\text{-}3}$ is a heterocyclic group or R$^1$, R$^2$ and/or R$^3$ taken together with their common nitrogen atom form a ring.

I. Salts of IPM and IPM Analogs

The compounds and compositions disclosed herein include IPM and IPM analogs that are formulated with one or more equivalents of a base. Because IPM and its analogs are acid labile and are acidic, the presently disclosed compounds offer greater stability as well as other advantages. The advantages of the disclosed formulations in terms of synthesis, stability and bioavailability will be apparent to those of ordinary skill in the art upon consideration of the present disclosure.

In one embodiment, the disclosed compounds are salts of isophosphoramide mustard or isophosphoramide mustard analogs including one or more cations. In one embodiment, the cations can be a conjugate acid of an amine base or can be a quaternary ammonium cation. Suitable counterions for isophosphoramide mustard and its analogs include the conjugate acids (as used herein terms that refer to amines should be understood to include their conjugate acids unless the context clearly indicates that the free amine is intended) of bases including basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions are examples of suitable counterions that can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl)methylamine, N,N-dimethyl-N-(2-hydroxyethyl)amino, tri-(2-hydroxyethyl)amine and N-methyl-D-glucamine.

In a further embodiment, the salts described above can include a second amine or ammonium group. In one embodiment the compounds disclosed herein include more than one equivalent of an amino for each equivalent of isophosphoramide mustard or isophosphoramide mustard analog. Such embodiments include those having non-integer ratios of amine to isophosphoramide mustard or isophosphoramide mustard analogs. In certain embodiments, the compounds have a two to one or three to one ratio of amine to isophosphoramide mustard or an isophosphoramide mustard analog. In working embodiments salts were produced containing two equivalents of amine base per equivalent of isophosphoramide mustard. In one embodiment, an amine base used to form isophosphoramide mustard and isophosphoramide mustard analog salts includes more than one amino group; such bases can be termed "multibasic." More specifically, certain examples of multibasic bases that can be used have two amino groups; such compounds can be referred to as "dibasic." For example, one suitable dibasic molecule is N,N-dimethylaminopyridine, which includes two basic amino groups. In a particular embodiment of a compound disclosed herein a compound includes isophosphoramide mustard or an isophosphoramide mustard analog and one equivalent of a dibasic amine.

In one embodiment, the disclosed compounds include one or more zwitterionic bases. Examples of such bases include basic amino acids, which are zwitterionic at physiological pH.

In one embodiment the presently disclosed salts are more stable than isophosphoramide mustard and isophosphoramide mustard analogs. For example, isophosphoramide mustard, following lyophilization of the pure compound, decomposes by nearly 40% during storage at −20° C. for three months. In contrast, the lysine salt of IPM does not exhibit any measurable decomposition, even after ten months under similar storage conditions.

In certain embodiments, the disclosed compounds are stabilized isophosphoramide mustard salts or stabilized isophosphoramide salt analogs, wherein the salt has a half-life at room temperature (e.g., about 23° C.) in the presence of water that is greater than a half-life of isophosphoramide mustard in the presence of water under the same conditions. In certain preferred such embodiments, an isophosphoramide mustard salt has a half-life that is equal to or greater than twice as long as isophosphoramide mustard in the presence of water, more preferably, equal to or greater than five times.

In certain embodiments, lyophilisates of disclosed compounds are more stable than a lyophilized preparation of isophosphoramide mustard. In certain preferred such embodiments, the lyophilisate of the disclosed compounds have a longer shelf life than a lyophilized preparation of isophosphoramide mustard itself, preferably at least twice as long, more preferably at least five times as long.

In certain embodiments, pharmaceutical compositions of pharmaceutically acceptable salts of IPM or its analogs (such as the compounds of the above formula) are more stable than an otherwise identical composition of isophosphoramide mustard itself (i.e., not in a salt form) under identical conditions. In certain preferred such embodiments, the disclosed compositions have a longer shelf life than the lyophilized preparation of isophosphoramide mustard, preferably at least twice as long, more preferably at least five times as long.

Certain isophosphoramide mustard and isophosphoramide mustard analog compounds disclosed herein include two leaving groups. Without limitation to theory, it is believed that the two leaving groups are displaced in vivo by biomolecular nucleophiles, such as nucleic acids and proteins, thereby cross-linking the biomolecules. The term "leaving group" refers to a group that can be displaced by a nucleophile. With reference to the presently disclosed compounds, leaving group refers to a group that can be displaced to form an aziridinium intermediate, or can be directly displaced by a biomolecular nucleophile, such as a nucleic acid nucleophile, to form, for example, a 7-alkylated guanidinium species. Examples of suitable leaving groups include the halogens and the sulfonates (—SO₂R). In one embodiment of the disclosed isophosphoramide analog salts, the compound is a "mixed" leaving group compound, including two different types of leaving groups, for example a halogen and a sulfonate or two different halogens, such as a bromide and a chloride. U.S. Pat. No. 6,197,760 to Struck teaches methods for making such mixed leaving group compounds.

One embodiment of the present disclosure concerns antihyperproliferative agents of the formula

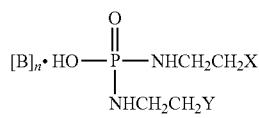

With reference to the formula, B can be, for each n, an independently selected basic molecule. In one embodiment of the formula, B can be selected from the basic amino acids, acyclic aliphatic amines, di- and tri alkyl amines, heterocyclic aliphatic amines, aromatic amines, substituted and unsubstituted pyridines, cyclic and acyclic guanidines, and cyclic and acyclic amidines. Typically, n is from 1 to about 3 such that the formula can include different basic molecules. With continued reference to the formula, X and Y are leaving groups. A person of ordinary skill in the art will understand that the illustrated isophosphoramide mustard structure includes an acidic proton, and as such exists predominantly as its conjugate base at physiological pH and in the presence of a base such as B. Likewise, B, being a basic group exists predominantly as its conjugate acid at physiological pH and in the presence of isophosphoramide mustard and isophosphomide mustard analogs. Exemplary embodiments of the disclosed compounds are depicted in Table 1.

TABLE 1

[B]$_n$• HO—P(=O)(NHCH$_2$CH$_2$X)—NHCH$_2$CH$_2$Y

| B | n | X | Y |
|---|---|---|---|
| lysine | 2 | Cl | Cl |
| NH$_3$ | 2 | Cl | Cl |
| cyclohexylamine | 2 | Cl | Cl |
| N-methyl-D-glucamine | 2 | Cl | Cl |
| N,-N-dimethylaminopyridine | 1 | Cl | Cl |
| arginine | 2 | Cl | Cl |
| lysine | 2 | Cl | —SO$_2$CH$_3$ |
| lysine | 2 | Br | —SO$_2$CH$_3$ |

In a further embodiment, the disclosed compounds include salts of isophosphoramide mustard. Certain examples of such isophosphoramide mustard salts can be represented by the formula

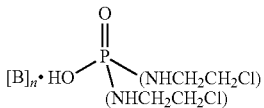

With reference to the formula above, B can be any basic group, particularly an amine. It should be recognized that the formula above will exist predominantly as the corresponding salt and thus can include compounds that are represented by the formula

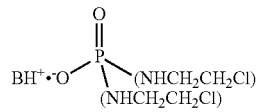

With reference to the formula above, such compounds also can include one or more additional equivalents of an amine or ammonium species. Such compounds can be represented by the formula

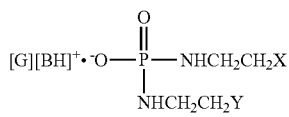

wherein G represents a second ammonium or amine species. In particular examples, G is a basic amino acid and BH$^+$ represents the conjugate acid of the same or a different basic amino acid.

In one embodiment BH$^+$ is the conjugate acid of G. In this embodiment, the disclosed isophosphoramide mustard salts can be represented by the formula

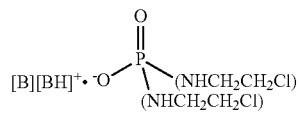

wherein B is an amine and BH$^+$ is its conjugate acid.

In one embodiment, the compounds disclosed herein include a metal cation, such as an alkali metal cation. Examples of such cations include Li$^+$, Na$^+$, K$^+$ and Rb$^+$ and Cs$^+$. In one aspect, such examples can be represented by the formula

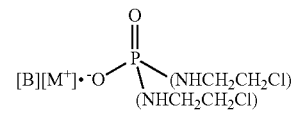

wherein M$^+$ represents an alkali metal cation and B is as defined above.

II. Compositions and Methods

Another aspect of the disclosure includes pharmaceutical compositions, preferably sterile pharmaceutical compositions, prepared for administration to a subject and which include a therapeutically effective amount of one or more of the currently disclosed compounds. Such sterile compositions may be prepared by passing a solution of the salt of IPM or an analog thereof through a sterile antimicrobial filter. Such sterile compositions preferably comprise the active ingredient of the invention with less than 10% degradation, preferably less than 5%, 2%, or even less than 1% decomposition as measured by assaying for the presence of decomposition by-products such as phosphoric acid and its salts and substituted ethylamines.

The compounds disclosed herein may be administered orally, topically, transdermally, parenterally, via inhalation or spray and may be administered in dosage unit formulations containing conventional non-toxic pharmaceutically acceptable carriers, adjuvants and vehicles.

Typically, parenteral administration of the disclosed isophosphoramide mustard salts and analogs thereof via injection is preferred. The inhibitors may be provided in a single dosage or chronically, dependent upon the particular disease, condition of patient, toxicity of compound and other factors as will be recognized by a person of ordinary skill in the art.

The therapeutically effective amount of the compound or compounds administered can vary depending upon the desired effects and the factors noted above.

Pharmaceutical compositions for administration to a subject can include carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In one embodiment, a disclosed compound is formulated for administration to a human subject. In aspect of this embodiment the pharmaceutical composition includes from about 0.1 mg/mL to about 250 mg/mL, such as from about 20 to about 100 mg/mL of the compound of an isophosphoramide mustard salt or analog thereof.

In one aspect, certain embodiments of pharmaceutical compositions are formulated into unit dosage forms. For example such unit dosage forms can contain from about 100 mg to about 1500 mg, such as from about 200 mg to about 1500 mg of a disclosed isophosphoramide mustard salt or analog thereof per dosage unit.

It is specifically contemplated in some embodiments that the present compounds are delivered via an injected and/or implanted drug depot, for instance comprising multi-vesicular liposomes such as in DepoFoam (SkyePharma, Inc. San Diego, Calif.) (see, for instance, Chamberlain et al. *Arch. Neuro.* 1993, 50, 261-264; Katri et al. *J. Pharm. Sci.* 1998, 87, 1341-1346; Ye et al., *J. Control Release* 2000, 64, 155-166; and Howell, *Cancer J.* 2001, 7, 219-227).

Methods are disclosed herein for treating conditions characterized by abnormal or pathological proliferative activity or neoplasia by administering one or more of the disclosed compounds and compositions to a subject "Neoplasia" refers to the process of abnormal and uncontrolled cell growth. Neoplasia is one example of a proliferative disorder. The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant."

Conditions that can be treated according to the disclosed method include those characterized by abnormal cell growth and/or differentiation, such as cancers and other neoplastic conditions. Typical examples of proliferative disorders that can be treated using the disclosed compounds and compositions are listed below.

Examples of hematological tumors that can be treated using the compounds and compositions disclosed herein include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Additional examples of conditions that can be treated using the disclosed compounds and compositions include solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma).

In one embodiment the compounds disclosed herein superior to CPA or Ifos alone against CPA resistant tumor growth. Therefore one aspect of a method disclosed herein includes treating a subject having a CPA resistant neoplastic condition with an isophosphoramide mustard salt or analog thereof disclosed herein.

In one embodiment of the method a subject is administered from about 0.2 mg/kg/day to about 20 mg/kg/day of a disclosed isophosphoramide mustard salt or analog thereof. For example, from about 0.5 to about 10 mg/kg/day, such as from about 1 to about 7.5 mg/kg/day of a disclosed compound can be administered to a subject.

In another embodiment of the method a subject is administered from about 10 to about 700 mg/m$^2$/day, such as from about 20 to about 400 mg/m$^2$/day or from about 100 to about 500 mg/m$^2$/day. For example, from about 30 to about 100 mg/m$^2$/day, such as from about 40 to about 90 mg/m$^2$/day of a compound disclosed herein.

In one embodiment of the method for treating hyper-proliferative disorders disclosed herein, a disclosed compound is administered to a subject on a multiple daily dosing schedule. In such embodiments the compound is administered on at least two days and on as many as five different days. In one aspect of multiple daily dosing schedules, the compound is administered to the subject on consecutive days, such as from two to five consecutive days.

In one embodiment of the method one or more additional therapeutic agents is administered to a subject in addition to the presently disclosed compounds and compositions. For example, additional therapeutic agents can that can be used include microtubule binding agents, DNA intercalators or cross-linkers, DNA synthesis inhibitors, DNA and/or RNA transcription inhibitors, antibodies, enzymes, enzyme inhibitors, gene regulators, and/or angiogenesis inhibitors.

"Microtubule binding agent" refers to an agent that interacts with tubulin to stabilize or destabilize microtubule formation thereby inhibiting cell division. Examples of microtubule binding agents that can be used in conjunction with the presently disclosed isophosphoramide mustard salts and analogs thereof include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and will be known to those of ordinary skill in the art. For example, suitable epothilones and epothilone analogs for incorporation into the present compounds are described in International Publication No. WO 2004/018478, which is incorporated herein by reference. Taxoids, such as paclitaxel and docetaxel are currently believed to be particularly useful as therapeutic agents in the presently disclosed compounds. Examples of additional useful taxoids, including analogs of paclitaxel are taught by U.S. Pat. No. 6,610,860 to Holton, U.S. Pat. No. 5,530,020 to Gurram et al. and U.S. Pat. No. 5,912,264 to Wittman et al. Each of these patents is incorporated herein by reference.

Suitable DNA and/or RNA transcription regulators, including, without limitation, actinomycin D, daunorubicin, doxorubicin and derivatives and analogs thereof also are suitable for use in combination with the presently disclosed compounds.

DNA intercalators and cross-linking agents that can be incorporated into the disclosed compounds include, without limitation, cisplatin, carboplatin, oxaliplatin, mitomycins, such as mitomycin C, bleomycin, chlorambucil, cyclophosphamide and derivatives and analogs thereof.

DNA synthesis inhibitors suitable for use as therapeutic agents include, without limitation, methotrexate, 5-fluoro-5'-deoxyuridine, 5-fluorouracil and analogs thereof.

Examples of suitable enzyme inhibitors for use in combination with the presently disclosed compounds include, without limitation, camptothecin, etoposide, formestane, trichostatin and derivatives and analogs thereof.

Suitable therapeutics for use with the presently disclosed compounds that affect gene regulation include agents that result in increased or decreased expression of one or more genes, such as, without limitation, raloxifene, 5-azacytidine, 5-aza-2'-deoxycytidine, tamoxifen, 4-hydroxytamoxifen, mifepristone and derivatives and analogs thereof.

The term "angiogenesis inhibitor" is used herein, to mean a molecule including, but not limited to, biomolecules, such as peptides, proteins, enzymes, polysaccharides, oligonucleotides, DNA, RNA, recombinant vectors, and small molecules that function to inhibit blood vessel growth. Angiogenesis is implicated in certain pathological processes, such as those involved in disorders such as diabetic retinopathy, chronic inflammatory diseases, rheumatoid arthritis, dermatitis, psoriasis, stomach ulcers, and most types of human solid tumors.

Angiogenesis inhibitors are known in the art and examples of suitable angiogenesis inhibitors include, without limitation, angiostatin K1-3, staurosporine, genistein, fumagillin, medroxyprogesterone, suramin, interferon-alpha, metalloproteinase inhibitors, platelet factor 4, somatostatin, thromobospondin, endostatin, thalidomide, and derivatives and analogs thereof.

Other therapeutic agents, particularly anti-tumor agents, that may or may not fall under one or more of the classifications above, also are suitable for administration in combination with the presently disclosed compounds. By way of example, such agents include adriamycin, apigenin, rapamycin, zebularine, cimetidine, and derivatives and analogs thereof.

III. Examples

The foregoing disclosure is further explained by the following non-limiting examples.

Example 1

This example describes the synthesis of the phenyl ester of IPM according to the scheme.

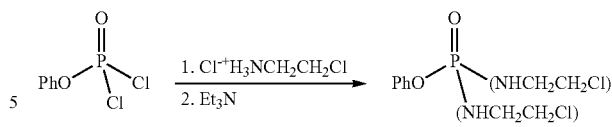

To a 5 L 3 neck round bottom flask equipped with a mechanical stirrer, a 500 mL drip funnel and a calcium chloride drying tube 2-chloroethylamine hydrochloride (116 g; 1.0 mol) is suspended in 1200 mL methylene chloride and stirred in an ice water bath. When the temperature fell to 5° C., phenyldichlorophosphonate (105.5 g; 0.5 mol) (commercially available from Aldrich, Milwaukee, Wis.) was added. Triethylamine (202 g, 2 mol) was dripped in slowly at 1 drop per second; the temperature did not exceed 5° C. The mixture is allowed to stir overnight. The following day, 200 mL concentrated hydrochloric acid (12 M) was mixed with 1800 mL water. To the reaction mixture was slowly added 200 mL of the acid solution. The mixture became clear and was transferred to a 2 L separatory funnel and the organic and aqueous layers separated. The organic layer was extracted with the acid solution 9×200 mL followed by water 1×200 mL. The organic layer was then separated and dried over sodium sulfate and filtered. The methylene chloride was then evaporated under reduced pressure and the oil residue was dissolved in 40 mL ethyl acetate and 60 mL hexane was slowly added with stirring; it was then covered with Parafilm and kept at 5° C. in a freezer overnight. The following day the white crystals were suction filtered and washed with 100 mL cold hexane and then allowed to air dry. The mother liquid was kept in the freezer for 9 hours and a second crop of crystals formed and these were allowed to air dry. A third crop of crystals formed on freezing the mother liquor from the second crop overnight and these were air-dried. The combined crops had a yield of 117.3 grams; 0.39 mol. The yield was 82%; m.p. 53-55; Anal. Calcd for $C_{10}H_{15}Cl_2N_2O_2P$ (F.W. 297.13) C, 40.44%; H, 5.09%; N, 9.43%. Found C, 39.7%; H, 4.97%; N, 9.00%.

Example 2

This example describes the synthesis of IPM (N,N'-di(2-chloroethyl)phosphorodiamidic acid) from the IPM phenyl ester described in example 1.

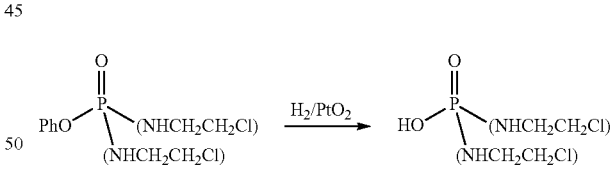

The white solid ester from example 1 (0.39 mol) was dissolved in 100 mL of 95% ethanol and added to a Parr flask and 2.5 g $PtO_2$ was added. The suspension was hydrogenated at 50 PSI; two hours later the hydrogenation was stopped and 2.5 g $PtO_2$ was cautiously added with stirring. Hydrogenation was resumed at 50 PSI for two hours. It was then stopped, brought to ambient pressure and heated on a hot plate with magnetic stirring. When the suspension was boiling it was suction filtered immediately through a 5.5 cm suction funnel with two filter papers and the supernatant stored at 5° C. for two hours; the catalyst is saved and added to the Parr flask and stored in a freezer overnight. The white solid that formed was suction filtered through a 9 cm suction funnel and saved in a pesticide free jar, the mother liquor was added to the Parr flask and 1.25 grams $PtO_2$ was added it was hydrogenated at 50 PSI for two hours. It was stopped, heated and filtered as before and the mother liquor kept in the freezer overnight. The white crystals that formed were suctioned filtered and combined with the first crop. The mother liquor is collected in the Parr flask with the used catalyst and an additional 1.25 grams of $PtO_2$ is added and hydrogenation is resumed at 50 PSI for 2 hours. It was then stopped, heated and filtered to produce a third crop, which was combined with crops 1 and 2. The combined crops were stirred in 150 mL of acetone for 30 minutes then stored at 5° C. for two hours and then filtered and stored in a vacuum desiccator for two hours. The yield was 38 g; 0.17 mol; 44% yield; mp(corr) 112-114. Anal. Calcd for $C_4H_{11}N_2O_2PCl_2$ (F.W. 221.11) C, 21.73%; H, 5.01%; N, 12.67%. Found C, 22.12%; H, 5.02%; N, 12.23%.

Example 3

This example describes the preparation of IPM lysine salt from IPM produced according to example 2. The L-lysine was weighed (26.4 g) and the water measured (6 L). The L-lysine is added to the water with stirring @2-8° C. The bulk drug substance, IPM, is weighed (20 g) and added slowly with stirring @2-8° C. to the lysine solution.

Once dissolved at 2-8° C., the solution is passed through a sterile antimicrobial filter (0.22 microns). The solution is maintained at 2-8° C. and dispersed into vials under sterile conditions.

The dissolved product is then lyophilized under the following conditions.

| Time (Hours) | Action | Temperature (° C.) |
|---|---|---|
| 0-1 | Loading | 0 –45 |
| 1-7 | Hold | –45 |
| 7-34 | Primary Dry | –25 |
| 34-55 | Secondary Dry | –10 |
| 55-76 | Secondary Dry | 0 |
| 76+ | Nitrogen purge | 0 |

Alternatively, the dissolved product may be lyophilized under the following conditions.

| Time (Hours) | Action | Temperature (° C.) |
|---|---|---|
| 0-0.5 | Loading | 0 –45 |
| 0.5-6.5 | Hold | –45 |
| 6.5-33 | Primary Dry | –25 |
| 33-54 | Primary Dry | –10 |
| 54-95 | Secondary Dry | 0 |
| 95+ | Nitrogen purge | 0 |

Figure 2:
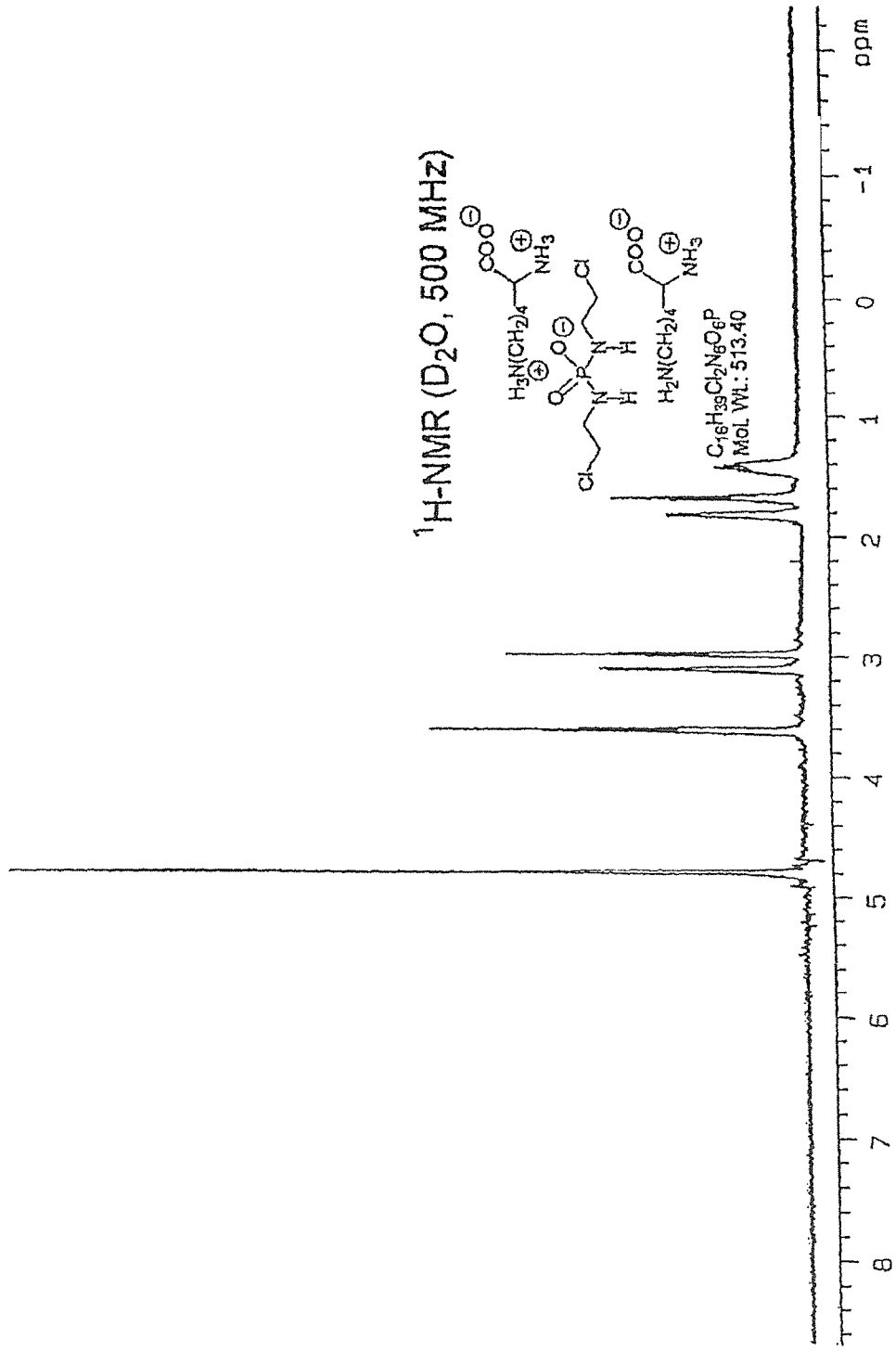
FIG. 2 is a $^1$H NMR spectrum of IPM.(LYS)$_2$ in D$_2$O recorded at 500 MHz.
Figure 3:
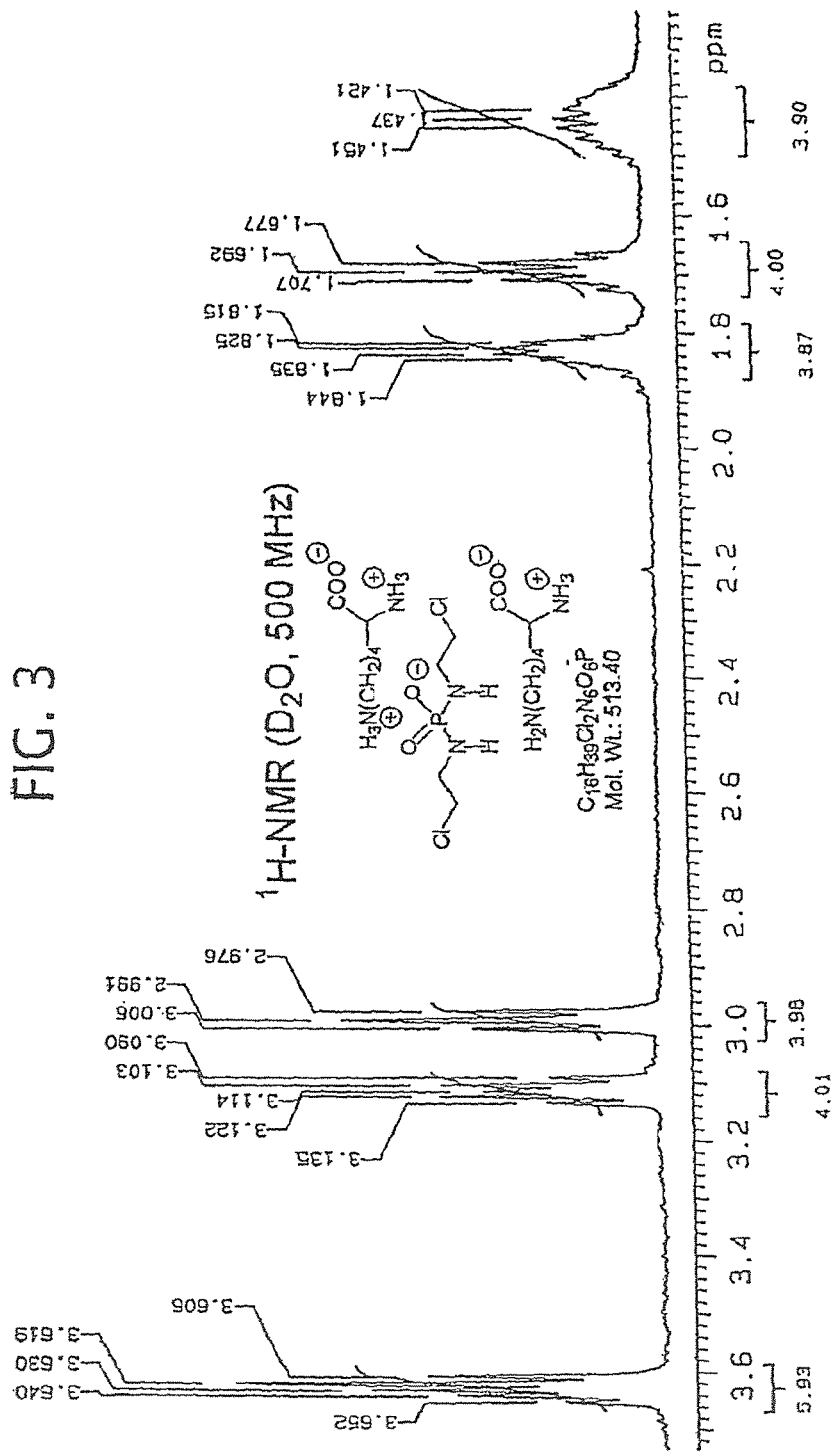
FIG. 3 is an expanded section of the spectrum in FIG. 2.
Figure 4:
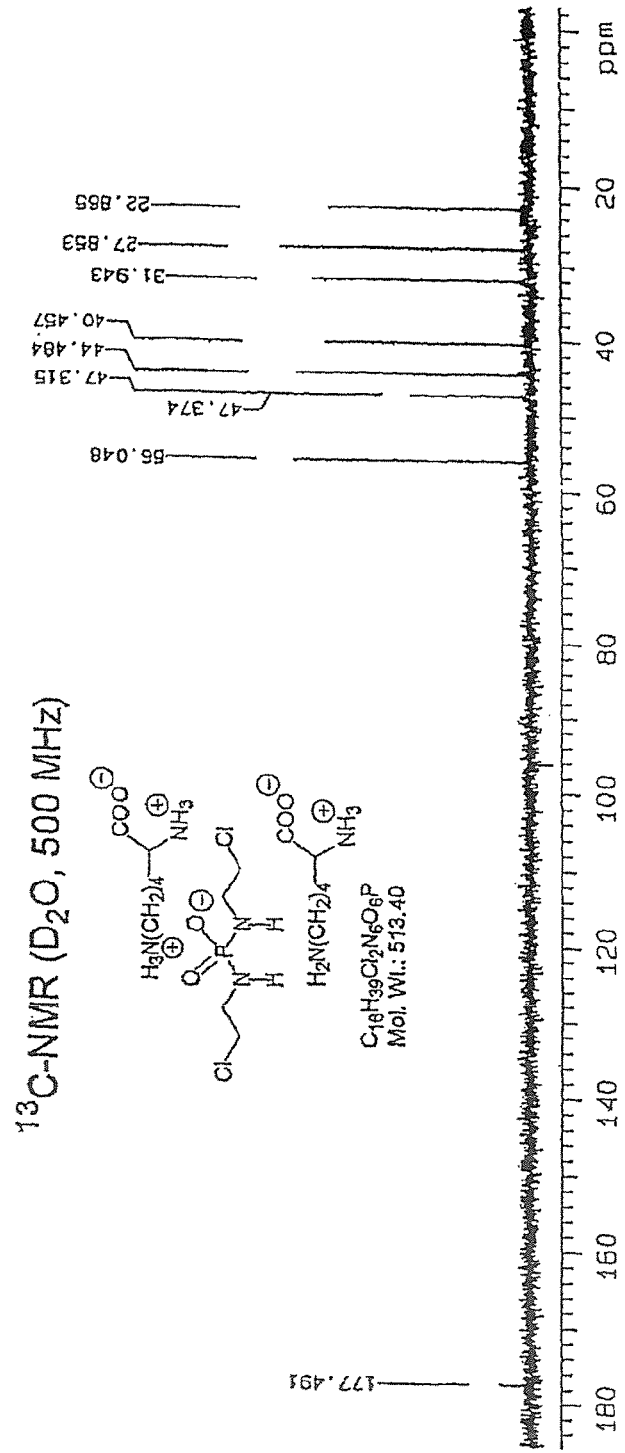
FIG. 4 is $^{13}$C NMR spectrum of IPM.(LYS)$_2$.

The vials are capped under sterile conditions according to standard operating procedure. The lyophilized IPM lysine salt is packaged in unprinted glass vials with crimped rubber sealed caps. This container/closure system doer not include a liner. Negative ion electrospray mass spectrometry revealed characteristic peaks for $IPM.(LYS)_2$ at M=219.0, 441.0 (dimer) and 662.7 mass units (trimer). The 1H NMR and $^{13}C$ NMR spectra of $IPM.(LYS)_2$ in $D_2O$ are provided as FIGS. 2-4.

The cyclohexyl amine and ammonium salts of IPM were prepared as described above for the lysine salt. Each of these salts was isolated having a 2:1 stoichiometry of amine:IPM.

Example 4

This example describes the evaluation of IPM against several different cancer cell lines implanted in mice. The mice tolerated intraperitoneal (IP) and intravenous (IV) treatment with IPM well in each study; the only toxicities are organ pathologies observed at autopsy that were associated with the induced tumors.

First, IPM was evaluated against two L1210 variants, L1210/0 and L1210/CPA cell lines implanted in mice, as compared with Ifos. The dosages for IPM were 50% of the dose for Ifos. ILS was observed for all three agents in the L1210/0 treated groups. However, for the L1210/CPA model, the IPM treatment demonstrated superiority over the other two arms (Ifos vs CPA). In the CPA resistant tumor line, the IPM treated animals had a two-fold increase in survival with a tumor burden reduction of 7. For the L1210/0 tumor model, IPM was equally active to CPA and Ifos, but at a lower dose. This demonstrates that CPA resistant cells are not cross-resistant to IPM. The results of this study are recorded below in Table 2.

TABLE 2

Activity of isophosphoramide mustard against L1210/0 and L1210/CPA leukaemias
(Optimal response at #$LD_{10}$ dose, from dose-response study)

| | | L1210/0† Tumor burden at start of $R_x = 8.5 \times 10^7$ cells | | | L1210/CPA† Tumor burden at start of $R_x = 6.0 \times 10^7$ cells | | |
|---|---|---|---|---|---|---|---|
| Agent | Dosage* (mg kg$^{-1}$) | Day 60 Survivors/ total | % ILS (dying mice only) | Net log$_{10}$ Reduction in tumor burden after therapy‡ | Day 60 survivors/ total | % ILS (dying mice only) | Net log$_{10}$ Reduction in tumor burden after therapy‡ |
| Cyclophosphamide | 200 | 0/10 | +107 | 7 | 0/10 | +57 | 4 |
| Ifosfamide | 431 | 0/10 | +185 | 8 | 0/10 | +85 | 5 |
|  | 289 | 0/9 | +114 | 8 | 0/10 | +57 | 4 |
| Isophosphoramide mustard | 100 | 0/10 | +128 | 8 | 1/10 | +114 | 7 |

*Treatment: IP; day 2 only; highest non-toxic dose ($LD_{10}$ or less) in a range of doses.
†IP; 10$^6$ cells, in male $CDF_1$ mice.

A second study demonstrates the inhibition of Lewis lung carcinoma by IPM in mice implanted with Lewis lung carcinoma tumors. Single second day IP dosings with CPA, Ifos, PM and IPM to mice bearing Lewis Lung carcinoma revealed that IPM yielded 6/10 tumor free survivors, as compared to 7/10 for Ifos and 5/10 for CPA at equitoxic, equal doses. The single dose schedule was used for each agent and the activities noted (T-C) were the same between all four agents.

The results of this study, recorded in Table 3, demonstrate that IPM is effective against Lewis lung carcinoma.

TABLE 3

Response of Lewis Lung Carcinoma to Isophosphoramide Mustard
Implant Size: 20-30 mg; Implant Site: s.c.; Drug Treatment: IP

| Agent | Schedule | Highest non-toxic dosage (mg kg$^{-1}$/dose) | Tumor-free survivors | T-C*† | % ILS‡ | Log kill totalδ |
|---|---|---|---|---|---|---|
| Cylophosphamide | Day 2 Single dose | 200 | 5/10 | 27 | 68 | >6.8 |
| Ifosfamide | Day 2 Single dose | 300 | 7/10 | 18 | 55 | >4.5 |
| Phosphoramide mustard | Day 2 Single dose | 200 | 0/10 | 4.9 | 15 | 1.2 |
| | Day 2 Q5 min × 7 | 30 | 0/10 | 6.1 | 17 | 1.5 |
| Isophosphoramide mustard | Day 2 Single dose | 100 | 6/10 | 8.4 | 34 | >2.1 |

*Tumor growth delay (T-C), where T = median time (days) required for the treatment-group tumors and C, the control group tumors (median of 120 each) to reach a predetermined weight (750 mg). Tumor-free survivors were excluded from these calculations.
†Control: Median day of death = 29; time for median tumor to reach 750 mg = 10.4 days; there were no tumor-free survivors among the 30 control mice.
‡Increase in life span, excluding survivors.
δThe Log$_{10}$ cell kill (total) was calculated from the following formula: Log kill = T-C value/(3.32 T$_4$). Where T$_4$ is the tumor volume-doubling time measured from a best fit straight line of the control-group tumors in exponential growth (100-400 mg range). T$_4$ = 1.2 for Lewis tumor in this experiment.

A third study evaluated the efficacy of IPM in the inhibition of B16 melanoma growth. Single dose administrations of IPM at 150 mg revealed that IPM was slightly inferior to CPA but better than Ifos in this resistant animal model. There were no statistical differences between % ILS responses between the three therapeutic agents. The results of this study, recorded in Table 4, demonstrate the efficacy of IPM against melanoma.

TABLE 4

A Comparison of the Response of s.c. B16 Melanoma to Cyclophosphamide, Isophosphoramide Mustard, Phosphoramide Mustard, and Ifosfamide

| Agent | Rx Schedule | Dosage (mg mg$^{-1}$) | Tumor-free survivors | T-C* (days) | % ILS |
|---|---|---|---|---|---|
| Cylophosphamide | Day 2 Single dose | 200 | 5/10 | 27 | 68 |
| Ifosfamide | Day 2 Single dose | 300 | 7/10 | 18 | 55 |
| Phosphoramide mustard | Day 2 Single dose | 200 | 0/10 | 4.9 | 15 |
| | Day 2 Q5 min x 7 | 30 | 0/10 | 6.1 | 17 |
| Isophosphoramide mustard | Day 2 Single dose | 100 | 6/10 | 8.4 | 34 |

*See footnote with Table 3, above. Predetermined weight was 750 mg.

A fourth study evaluated IPM in the inhibition of P388 Leukemia in mice. In this animal model, IPM was comparably effective to CPA and Ifos against IP implanted P388 leukemia as indicated by >log$_{10}$ cell kill, although it produced fewer tumor-free survivors. However, with the P388/CPA tumor model, there was significantly improved cell kill as well as % ILS for IPM as compared to CPA and Ifos. The results of this study are recorded in Table 5. All data is statistically significant and demonstrates that IPM can be used against CPA resistant or treated tumors as well as for patients pretreated with other agents.

TABLE 5

Activity of isophosphoramide mustard against P388/0 and P388/CPA leukaemias
(Optimal response at #LD$_{10}$ dose, from dose-response study)

| Agent | Dosage* (mg kg$^{-1}$) | P388/0† Tumor burden at start of R$_x$ = ~4.4 × 10$^6$ cells | | | P388/CPA† Tumor burden at start of R$_x$ = ~4.6 × 10$^6$ cells | | |
|---|---|---|---|---|---|---|---|
| | | Day 60 survivors/ total | % ILS (dying mice only) | Net log$_{10}$ reduction in tumor burden after therapy‡ | Day 60 survivors/ total | % ILS (dying mice only) | Net log$_{10}$ Reduction in tumor burden after therapy‡ |
| CPA | 265 | 7/10 | +280 | 7 | 0/10 | +35 | 3 |
| | 175 | 4/10 | +130 | 7 | 0/10 | +35 | 3 |
| Ifos | 538 | 7/10 | +210 | 7 | 0/10 | +42 | 4 |
| | 431 | 7/10 | +130 | 7 | 0/10 | +39 | 4 |
| IPM | 125 | 0/9 | +100 | 6 | 0/10 | +71 | 7 |
| | 100 | 1/10 | +140 | 7 | 0/10 | +85 | 7 |

*Treatment: IP; day 1 only; highest non-toxic dose (LD$_{10}$ or less) in a range of doses.
†Implant: IP; 10$^6$ cells, in female CDF$_1$ mice.

A fifth study evaluated the inhibition of implanted M5076 sarcoma with IPM in mice. IPM in doses of 18-40 mg/kg were injected IP to growing tumors daily for five days (the compound was injected IP daily on days 11-15). T-C was 6.1 days at 40 mg/kg. The doses were tolerated well with significant improvement in response. The mice tolerated the IP treatments well; the only toxicities are organ pathologies observed at autopsy that were associated with the induced tumors. The results of this study, recorded in Table 6, demonstrate that IPM is effective against sarcoma in a dose-dependent fashion.

TABLE 6

Response of SC Implanted M5076 Sarcoma to Treatment with IPM

| Agent | Dose (mg/kg) | Days To 2 doublings | Days Delay (T-C) |
|---|---|---|---|
| IPM | 40 | 15.4 | 6.1 |
| IPM | 27 | 12.6 | 3.3 |
| IPM | 18 | 10.3 | 1 |

A sixth study evaluated the inhibition of implanted 16/C mammary tumors in mice. Mice were implanted with the 16/C mammary tumor, and when the tumors were palpable/measurable, were treated with CPA, Ifos and IPM, as individual agents. CPA and Ifos were used as controls for IPM. The drugs were administered IP in doses of 30-60 mg/kg/per day for 4 days, starting on day 7 after tumor implantation. There was statistical improvement in activity for IPM as compared to CPA and Ifos, at all doses for the three agents. IPM was superior in 'days to 2 doublings' and 'days delay (T-C)' when compared to Ifos and CPA at the same dosage/day against this aggressive murine mammary tumor. All ratios were within confidence limits. These data (recorded in Table 7) demonstrate the efficacy of IPM against mammary tumors and the four day dosings further support the superiority of multiple dosings for IPM.

TABLE 7

Response of SC 16/C Mammary Tumor to Treatment with CPA, IFOS, and IPM

| Agent | Dose (mg/kg) | Route | Schedule | | Days to 2 Doublings | Days Delay (T-C) |
|---|---|---|---|---|---|---|
| Control | | IP | Q 1 dx 4 day 7 | CONTROL | 3.2 | |
| CPA | 60 | IP | Q 1 dx 4 day 7 | CPA | 7.7 | 4.5 |
| CPA | 50 | IP | Q 1 dx 4 day 7 | | 7.2 | 4.0 |
| CPA | 40 | IP | Q 1 dx 4 day 7 | | 4.4 | 1.2 |
| CPA | 30 | IP | Q 1 dx 4 day 7 | | 3.6 | 0.4 |
| IFOS | 60 | IP | Q 1 dx 4 day 7 | IFOS | 4.6 | 1.4 |
| IFOS | 50 | IP | Q 1 dx 4 day 7 | | 4.9 | 1.7 |
| IFOS | 40 | IP | Q 1 dx 4 day 7 | | 3.8 | 0.6 |
| IFOS | 30 | IP | Q 1 dx 4 day 7 | | 4.0 | 0.8 |
| IPM | 50 | IP | Q 1 dx 4 day 7 | IPM | 9.5 | 6.3 |
| IPM | 40 | IP | Q 1 dx 4 day 7 | | 8.5 | 5.2 |
| IPM | 30 | IP | Q 1 dx 4 day 7 | | 7.4 | 4.2 |

A seventh study evaluated IPM against IP implanted human lox-IMVI melanoma. Nude mice were implanted IP with the human Lox melanoma and treated for five days with either CPA or IPM. Doses for both were 40 mg/kg daily IV×5 days. % ILS was +121 for CPA and +52 IPM. However, excellent responses were seen and doses were well tolerated. Responses were within confidence levels. The results of this study (recorded in Table 8) demonstrate the efficacy of IV administration of IPM and further demonstrates the efficacy of IPM against human melanoma.

TABLE 8

| Treatment: IV; Q1DX5 (1) | | Therapeutic Response | |
| --- | --- | --- | --- |
| Agent | Dosage (mg/kg/dose) | Median Day of Death | % ILS |
| Control | — | 19.0 | — |
| CPA | 40 | 42.0 | +121 |
| IPM | 40 | 29.0 | +52 |

An eighth study evaluated the inhibition of human MX-1 mammary tumors with IPM. Daily IP administration of CPA, Ifos or IPM was compared in 40-60 mg/kg dosing on a schedule of daily×5 days beginning with day 12 (after implantation). The data recorded in Table 9 demonstrate that IPM is active against human mammary tumors. All ratios were in competence limits.

TABLE 9

Response of SC MX-1 Mammary Tumor to Treatment with CPA, IFOS, and IPM

| Agent | Dose (mg/kg) | Route | Schedule | Days to 2 doublings | Days Delay (T-C) |
| --- | --- | --- | --- | --- | --- |
| CPA | 60 | IP | Q 1dx 5 day 12 | >48.0 | >40.5 |
| IFOS | 60 | IP | Q 1dx 5 day 12 | 39.4 | 31.9 |
| IFOS | 40 | IP | Q 1dx 5 day 12 | 16.1 | 8.6 |
| IPM | 60 | IP | Q 1dx 5 day 12 | 26.5 | 19.0 |
| IPM | 40 | IP | Q 1dx 5 day 12 | 14.2 | 6.7 |

Example 5

This example compares the efficacy of IPM and that of IPM.(LYS)$_2$ and IPM.(NH$_4$)$_2$ salt against various hyperproliferative cell lines.

The efficacy of IPM and IPM.(LYS)$_2$ salt and IPM.(NH$_4$)$_2$ salt against Lewis lung murine tumor was compared when the compounds were administered by IP routes daily for 5-days in doses of 20-125 mg/kg daily×5 days, beginning with day 6 (after implantation). IPM and its lysine salt possessed equivalent activities at doses that reflected a 2-fold increase for the MTD (mg/kg/dose) of the salt over parent drug. All ratios were within confidence limits. The mice tolerated IP administration of the salt well; the only toxicities are organ pathologies observed at autopsy that were associated with the induced tumors. The results of this study (recorded in Table 10) demonstrate that IPM.(LYS)$_2$ exhibits equivalent efficacy to IPM against Lewis lung murine tumor, and that the IPM.(NH$_4$)$_2$ salt is effective against Lewis lung murine tumor.

TABLE 10

Lewis Lung Murine Tumors

| Agent | MTD Dosage (mg/kg/dose) | T-C (days) |
| --- | --- | --- |
| IPM lysine salt | 93.2 | 8.3* |
| IPM ammonium salt | 42.8 | 9.1 |
| IPM | 40.0 | 12.5* |

Implant: 20-30 mg tumor fragments
Treatment Route: Intraperitoneal
Schedule: q1d x 5 starting day 6
*Although the T-C values are statistically different (P = 0.004), the antitumor activities are comparable.

A second comparison of the efficacy of IPM, IPM.(LYS)$_2$ salt and IPM.(NH$_4$)$_2$ salt was conducted with respect to inhibition of MX-1 mammary tumors. In this study, the effects of IPM and IPM.(LYS)$_2$ salt were compared when administered IP, in doses of 20-100 mg/kg daily×5 days, beginning with day 12 following implantation of MX-1 mammary tumors in mice. IPM.(LYS)$_2$ salt was 8-fold superior to IPM at comparable dosing. The MTD was also higher for the lysine salt. All ratios were within confidence limits. The mice tolerated the IP treatment with IPM.(LYS)$_2$ and IPM.(NH$_4$)$_2$ salts well; the only toxicities are organ pathologies observed at autopsy that were associated with the induced tumors. This data (recorded in Table 11) demonstrates that both IPM.(LYS)$_2$ salt and IPM.(NH$_4$)$_2$ salt are significantly superior to IPM against human breast tumor cells.

TABLE 11

MX-1 Human Breast Tumor

| Agent | MTD Dosage (mg/kg/dose) | T-C (days) |
| --- | --- | --- |
| IPM lysine salt | 93.2 | 10.2* |
| IPM ammonium salt | 28.6 | 4.6 |
| IPM | 40.0 | 2.1* |

Implant: 20-30 mg tumor fragments subcutaneously in the mammary fat pad
Treatment Route: Intraperitoneally
Schedule: q1d x 5 starting day 12
*P-value = 0.041

Example 6

This example describes the evaluation the acute toxicity of isophosphoramide mustard lysine salt, following three days of daily intravenous (bolus) injection in mice. This study consisted of two phases.

First, the dose range-finding phase consisted of four treatment groups (one mouse/sex/group) that received the test article as a single daily dose for three consecutive days at respective dose levels of 100, 200, 400, and 600 mg/kg. The vehicle was 0.9% sodium chloride for injection, USP and all doses were at a constant volume of 15 mL/kg. The animals were observed for seven days following dosing. On Day 10, following the seven-day observation period, all surviving dose range-finding phase are presented in Appendix F of this report. Based on the deaths noted in the dose range-finding phase at 200, 400, and 600 mg/kg, the dose levels chosen for the main study phase were 50, 75, 100, 200, 300, 500, and 600 mg/kg (see below).

The second, main study phase consisted of eight treatment groups (five mice/sex/group) that received the test article as a single daily dose for three consecutive days at respective dose levels of 50, 75, 100, 200, 300, 400, 500, and 600 mg/kg. An additional group (5 mice/sex) served as a parent compound control and received the isophosphoramide mustard parent compound in the same manner, at a dose level of 150 mg/kg. The vehicle was 0.9% sodium chloride for injection, USP and all doses were at a constant volume of 15 ml/kg. The animals were observed for 11 days following the three-day dosing period.

Observations for mortality, morbidity, and the availability of food and water were conducted twice daily for all animals. Observations for clinical signs were conducted daily during the study (approximately one and four hours postdose on Days 1, 2, and 3, and once daily on non-dosing days). Body weights for all surviving animals were measured and recorded the second day after receipt, prior to randomization, and on Days −1 and 7. Body weights also were measured on all surviving main study phase animals on Day 14. Macroscopic evaluations were performed on each main study animal at necropsy (Day 15).

Animal Acquisition and Acclimation:

A total of 62 male and 61 female CrI: CD-1(1CR) BR mice (approximately six weeks old) were received from Charles River Laboratories, Portage, Mich., on Apr. 21, 2003. During the seven- to 16-day acclimation period, the sex of the animals was verified, the animals were weighed and observed twice daily with respect to general health and any signs of disease. At receipt, the animals were housed three to four mice/cage in order to acclimate to the automatic watering system. Three days after receipt, the animals were housed individually. All animals were given a detailed clinical observation prior to selection for study.

Randomization, Assignment to Study, and Maintenance:

Prior to assignment to study, the mice were weighed and examined for evidence of disease and other physical abnormalities. Animals assigned to the study had body weights within 20% of the mean body weight for each sex. Using a simple randomization procedure, the animals were placed into the treatment groups. Extra animals obtained for this study were euthanized via carbon dioxide inhalation and discarded.

Forty-nine male and 49 female mice (weighing 24.8 to 29.1 g and 21.5 to 24.2 g, respectively, at randomization) were assigned to the treatment groups identified in Table 12.

Each animal was assigned an animal number to be used in Provantis™ and was implanted with a microchip bearing a unique identification number. The individual animal number, implant number, and study number comprised a unique identification for each animal. The cage was identified by the animal number, study number, group number, and sex. Animal identification was verified during the course of the study as documented in the data.

The animals were individually housed in suspended, stainless steel, wire-mesh type cages. Fluorescent lighting was provided for approximately 12 hours per day and controlled via an automatic timer. Temperature and humidity were monitored and recorded daily, and maintained between 68 to 74° F. and 30 to 68%, respectively.

The dose levels for the dose range-finding phase were selected on the basis of available data from previous studies. The dose levels for the main study phase were set following a review of the results from the dose range-finding phase, with the exception of the 150 mg/kg parent compound control group, whose dose level was selected on the basis of available data from previous studies.

TABLE 12

Group Assignments

| Group Number | Dose Level (mg/kg) | Number of Animals Male | Number of Animals Female |
|---|---|---|---|
| Dose Range-finding Phase[a] | | | |
| 1 | 100 | 1 | 1 |
| 2 | 200 | 1 | 1 |
| 3 | 400 | 1 | 1 |
| 4 | 600 | 1 | 1 |
| Main Study Phase[b] | | | |
| 5[c] | 150 | 5 | 5 |
| 6 | 50 | 5 | 5 |
| 7 | 75 | 5 | 5 |
| 8 | 100 | 5 | 5 |
| 9 | 200 | 5 | 5 |

TABLE 12-continued

Group Assignments

| Group Number | Dose Level (mg/kg) | Number of Animals Male | Number of Animals Female |
|---|---|---|---|
| 10 | 300 | 5 | 5 |
| 11 | 400 | 5 | 5 |
| 12 | 500 | 5 | 5 |
| 13 | 600 | 5 | 5 |

[a] Animals were dosed for three days, followed by a seven-day observation period.
[b] Animals were dosed for three days, followed by a 11-day observation period.
[c] This group was dosed with Isophosphoramide Mustard Parent Compound (Parent Compound Control).

Administration:

Four range-finding treatment groups (one mouse/sex/group) received the test article as a single daily dose for three consecutive days via intravenous (bolus) injection at respective dose levels of 100, 200, 400, and 600 mg/kg. All doses were at a volume of 15 mL/kg and based on the most recent body weights.

Eight main study treatment groups received the test article as a single daily dose for three consecutive days via intravenous (bolus) injection at respective dose levels of 50, 75, 100, 200, 300, 400, 500, and 600 mg/kg. An additional group (five mice/sex) served as a parent compound control and received the Isopbhosphoramide Mustard Parent Compound in the same manner at a dose level of 150 mg/kg. All doses were at a volume of 15 mL/kg and based on the most recent body weight.

While the animal was restrained, the dosing formulation was administered through a needle that was inserted into the tail vein and the hub of the needle was observed for the presence of blood to ensure the proper placement of the needle in the vein. The dose was then administered at the absolute dose volume for each animal.

Observation and Examination:

All mice were observed for morbidity, mortality, injury, and the availability of food and water twice daily throughout the duration of the study.

A detailed clinical examination of each animal was performed at one and four hours postdose on Days 1, 2, and 3, and once daily on non-dosing days. The observations included, but were not limited to, evaluation of the skin, fur, eyes, ears, nose, oral cavity, thorax, abdomen, external genitalia, limbs and feet, respiratory and circulatory effects, autonomic effects such as salivation, and nervous system effects including tremors, convulsions, reactivity to handling, and bizarre behavior.

Body weights for all surviving animals were measured and recorded the second day after receipt, prior to randomization, and on Days −1 and 7. Body weights also were measured on all surviving main study phase animals on Day 14. The body weights recorded after receipt and prior to randomization are not reported, but are maintained in the study file.

On Day 10, all surviving dose range-finding phase animals were euthanized and discarded. No necropsies were conducted on any dose range-finding animals. All main study animals received a complete necropsy examination under procedures approved by a veterinary pathologist. At the termination of the study, all surviving main study phase animals were euthanized by carbon dioxide inhalation and exsanguination via abdominal vena cava.

Each animal was examined carefully for external abnormalities including masses. The skin was reflected from a ventral midline incision and any subcutaneous abnormalities were identified and correlated with antemortem findings. The abdominal, thoracic, and cranial cavities were examined for abnormalities and the organs were removed and examined. All abnormalities were recorded. No tissues were saved and the carcasses were discarded.

Statistics:

When appropriate, the $LD_{50}$ and the $LD_{10}$ and their 95% confidence limits were calculated using the Probit Procedure (SAS Institute, Inc. SAS/STAT® User's Guide, Version 6, Fourth Edition, Volume 2. Cary N.C.: SAS Institute; 1989) in SAS® (main study treated groups).

The computer systems used during the conduct of this study are presented in Table 13.

TABLE 13

Computer Systems

| | |
|---|---|
| In-life System: | Provantis ™ |
| Randomization: | Provantis ™ |
| Pathology: | Provantis ™ |
| Statistical Analyses: | SAS |
| Reporting: | SAS and Microsoft Office Professional |

Results:

The following data are the results of the definitive main study phase.

A summary of mortality results is presented in the Table 14 below. The mortality results generally exhibit a typical dose-response effect, with IPM Lysine Salt being slightly more toxic in females than in males. The IPM parent compound control group exhibited the expected mortality, as well as greater toxicity in females than males, correlating with available data from previous studies.

No treatment-related macroscopic findings were noted in either sex in postmortem observations.

Conclusions:

Mortality results generally displayed a typical dose-response effect, with IPM Lysine Salt being slightly more toxic in females than in males. No animals died at 50 or 75 mg/kg, 1 of 10 animals died at 100 mg/kg, 3 of 10 animals died at 200 mg/kg, 9 of 10 animals died at 300 mg/kg, and all animals died at 400, 500, and 600 mg/kg. The IPM parent compound control group exhibited the expected mortality (5 of 10 animals died), as well as greater toxicity in females than males, correlating with available data from previous studies. The onset of death on study was slightly delayed, with the first mortalities occurring on Day 6 and the last on Day 12. Clinical signs generally reflecting the deteriorating state of mice prior to death were observed in both sexes. Those clinical signs included moribundity, decreased activity, increased activity, swelling (tail, nose/muzzle, and/or face), breathing rapid/slow/shallow/difficult/audible, tremors, skin cold to touch, unkempt appearance, posture hunched, limb function impaired, hair discoloration in the dorsal and/or anogenital regions, feces few/absent, and urination decreased. Treatment-related decreases in mean body weight gain, or in may cases body weight loss, were noted in surviving animals by Day 7, with at least partial recovery by Day 14 in those animals surviving to study termination. No treatment-related macroscopic findings were noted at necropsy.

Based on the condition and findings of this study, the intravenous $LD_{10}$ of IPM 2Lys was calculated to be 133 mg/kg (95% confidence limits of 65 to 172) in mice (combined sexes), while the intravenous $LD_{50}$ was calculated to be 220 mg/kg (95% confidence limits of 184 to 265 mg/kg).

TABLE 14

Mortality by Day of Study and Cumulatively

| Dose Level | Study Day (Male/Female) | | | | | | | | | | | | | | | | Cumulative Mortality | |
|---|---|---|---|---|---|---|---|---|---|---|---|---|---|---|---|---|---|---|
| | 1 to 5 | | 6 | | 7 | | 8 | | 9 | | 10 | | 11 | | 12 to 14 | | | |
| (mg/kg) | M | F | M | F | M | F | M | F | M | F | M | F | M | F | M | F | M | F | Total |
| 150[a] | 0 | 0 | 0 | 1 | 0 | 1 | 0 | 2 | 0 | 0 | 0 | 0 | 1 | 0 | 0 | 0 | 1/5 | 4/5 | 5/10 |
| 50 | 0 | 0 | 0 | 0 | 0 | 0 | 0 | 0 | 0 | 0 | 0 | 0 | 0 | 0 | 0 | 0 | 0/5 | 0/5 | 0/10 |
| 75 | 0 | 0 | 0 | 0 | 0 | 0 | 0 | 0 | 0 | 0 | 0 | 0 | 0 | 0 | 0 | 0 | 0/5 | 0/5 | 0/10 |
| 100 | 0 | 0 | 0 | 0 | 0 | 0 | 0 | 0 | 1 | 0 | 0 | 0 | 0 | 0 | 0 | 0 | 1/5 | 0/5 | 1/10 |
| 200 | 0 | 0 | 0 | 0 | 0 | 0 | 0 | 0 | 0 | 0 | 0 | 2 | 0 | 0 | 0 | 1[b] | 0/5 | 3/5 | 3/10 |
| 300 | 0 | 0 | 0 | 1 | 1 | 3 | 1 | 0 | 0 | 0 | 1 | 1 | 1 | 0 | 0 | 0 | 4/5 | 5/5 | 9/10 |
| 400 | 0 | 0 | 0 | 4 | 3 | 1 | 1 | 0 | 0 | 0 | 0 | 1 | 0 | 0 | 0 | 0 | 5/5 | 5/5 | 10/10 |
| 500 | 0 | 0 | 4 | 2 | 1 | 3 | 0 | 0 | 0 | 0 | 0 | 0 | 0 | 0 | 0 | 0 | 5/5 | 5/5 | 10/10 |
| 600 | 0 | 0 | 3 | 5 | 2 | 0 | 0 | 0 | 0 | 0 | 0 | 0 | 0 | 0 | 0 | 0 | 5/5 | 5/5 | 10/10 |

[a]Parent Compound Control
[b]Death occurred on Day 12
M-Male
F-Female

The intravenous $LD_{10}$ of IPM Lysine Salt was calculated to be 133 mg/kg (95% confidence limits of 65 to 172) in mice (combined sexes), while the intravenous $LD_{50}$ was calculated to be 220 mg/kg (95% confidence limits of 184 to 265 mg/kg).

The $LD_{10}$ values for males and females separately were 140 and 179 mg/kg, respectively (95% confidence limits of 12 to 199 mg/kg for males; could not be calculated for females), while the $LD_{50}$ values for males and females were 247 and 197 mg/kg, respectively (95% confidence limits of 187 to 330 for males; could not be calculated for females).

Example 7

This example summarizes the results of extensive pre-clinical data for the toxicity of IPM and its lysine salt. This data is used to design dosage regimens for human clinical trials.

The toxicity of IPM and its lysine salt have been investigated through pre-clinical acute and sub-acute studies using mice, rats and dogs. Single dose oral, intravenous (IV) and intraperitoneal (IP) routes of administration for IPM have been studied in mice and rates. Multiple daily dose administrations—IV and IP—have been studied in mice and dogs. Sub-acute intravenous (3-day) dosing in the mouse and dog has provided the toxicology/pharmacokinetic information regarding toxicities and drug disturbances that were utilized in designing the administration and dose schedules in humans. Sub-acute IV (3-day) dosing with the IPM lysine salt was conducted in the mouse.

Based upon the results of the dose range finding study, higher doses of IPM were required to produce mortality than anticipated. For rats, the oral $LD_{50}$ values were calculated to be 4443 mg/kg for males, 2786 mg/kg for females and 3560 mg/kg for both sexes combined. In each case, the 95% confidence limits could be calculated.

For mice, oral $LD_{50}$ values were calculated to be 1014 mg/kg for males (95% confidence limits), 1962 mg/kg for females (95% confidence limits of 1523-2983 mg/kg) and 1432 mg/kg for both sexes combined (95% limits of 1128-1742 mg/kg).

For rats, single dose intravenous $LD_{50}$ values were calculated to be 567 mg/kg for males, 400 mg/kg for females and 428 mg/kg for both sexes combined. In each case, the 95% confidence limits could not be calculated. For mice, intravenous $LD_{50}$ values were calculated to be 929 mg/kg for males (95% confidence limits), 484 mg/kg for females (95% confidence limits of 72-1364 mg/kg) and 688 mg/kg for both sexes combined (95% confidence limits of 398-1366 mg/kg).

Administration of IPM by IV and IP routes did result in acute deaths for mice, rats and dogs. Oral administration to mice and rats was also evaluated and $LD_{50}$ values were determined in the 1.4-3.5 g/kg range for these rodent species. Acute intravenous toxicity symptoms in mice, rats and dogs, included less appetite, diarrhea, decreased activity and death.

The acceptable doses from the three (3) day dosing studies were significantly different from the single dose schedule. The effects of the drug on bone marrow, spleen and renal tubular functions were evaluated. The impact of IPM on these organs appears to contribute to the cause of death in these two species. A summary is presented below.

A sub-acute IV study of IPM in mice provided information as to $LD_{10}$ values and toxicity that could occur in humans. The mortality results displayed a typical dose-response effect, with IPM being slightly more toxic in females than in males.

The intravenous $LD_{10}$ of IPM was calculated to be 119 mg/kg (with 95% confidence limits of 87-134 mg/kg) in mice (combined sexes), while the intravenous $LD_{50}$ was calculated to be 149 mg/kg (with 95% confidence limits of 132-169 mg/kg). The $LD_{10}$ values for males and females separately were 168 and 125 mg/kg, respectively, while the $LD_{50}$ values for males and females were 176 and 132, respectively. In each case, the 95% confidence limits could not be calculated.

The sub-acute IPM lysine salt study included a total of 40 male and 40 female mice (CrI: CD-1(1CR)BR) weighing 24.8 to 29.1 g and 21.5 and 24.2 g, respectively, at randomization) were treated with doses of 50 to 600 mg/kg IV daily×3 days (Table 8.8).

For IPM LYS salt, the intravenous $LD_{10}$ for the 3-day mouse study was calculated to be—133 mg/kg (95% confidence limits 65 to 172 mg/kg (combined sexes)), while the intravenous $LD_{50}$ was 220 mg/kg (with 95% confidence limits of 184 to 265 mg/kg (for combined sexes)). The $LD_{10}$ values for males and females separately were 140 and 179 mg/kg, respectively (95% confidence limits of 12 to 199 mg/kg for males; could not be calculated for females). The $LD_{50}$ values for males and females were 247 and 197 mg/kg, respectively (95% confidence limits of 187 to 330 for males; could not be calculated for females).

The IPM lysine salt generally displayed a typical dose-response effect, with slightly more toxicity seen in females. No mice died at 50, 75 or 200 mg/kg, 1 of 10 animals died at 100 mg/kg, 9 out of 10 animals died at 300 mg/kg, and all mice died at 400, 500, and 600, mg/kg. The parent IPM control group exhibited the expected mortality, as well as greater toxicity in females than males, correlating with available data from previous studies. The onset of death on study was slightly delayed, with the first mortalities occurring on Day 6 and the last on Day 12. Clinical signs generally reflecting the deteriorating state of mice prior to death were observed in both sexes.

Based on the findings of microscopic examination, IPM administered alone or as the lysine salt IV daily for three days produced treatment-related bone marrow depletion, kidney tubular necrosis, or a combination of both and were considered the cause of death. For IPM, severe bone marrow depletion was present in males at 178 mg/kg and higher, and in females at 133 mg/kg and higher. Kidney tubular necrosis occurred in males at 237 mg/kg and higher, and in females at 133 mg/kg and higher. In addition, splenic lymphoid depletion was noted in most males and in all females that died during the study. No obvious treatment-related microscopic findings were noted in either sex at 75 mg/kg. Clinical signs generally secondary to the deteriorating state of the mice prior to death were observed but no clear evidence of body weight effects were seen in mice surviving to study termination.

The intravenous $LD_{10}$ for isophosphoramide mustard (IPM) and its lysine salt administered daily for three days were calculated to be 119 mg/kg vs. 133 mg/kg, respectively, with $LD_{50}$ calculated as 149 mg/kg vs. 220 mg/kg, respectively.

Acute and sub-acute toxicity studies in rodents and dogs have been performed with IPM and its lysine salt. These studies also have been used to develop acceptable starting doses human investigations. A summary of the rodent and dog toxicity data for IV administration of IPM is recorded in Table 15 and a summary of the mouse toxicity data for IV administration of IPM.(LYS)$_2$ is recorded in Table 16.

TABLE 15

Summary of Intravenous Treatment Experience - IPM

| # and Specie | Dose, Regimen and Duration | Total Dose of IPM (mg) | Plasma IPM | Efficacy | Safety $LD_{50}$ (mg/kg) |
|---|---|---|---|---|---|
| 47 Rats | 400-2,000 mg/kg; Iv x 1 d | 81.6-650 | Not Tested | Not Tested | 428 |
| 40 Mice | 100-1,200 mg/kg; Iv x 1 d | 3.2-36 | Not Tested | Not Tested | 688 |
| 80 Mice | 75-562 mg/kg; iv daily x 3 days | 5.7-60.6 | Not Tested | Not Tested | 149 |

TABLE 15-continued

Summary of Intravenous Treatment Experience - IPM

| # and Specie | Dose, Regimen and Duration | Total Dose of IPM (mg) | Plasma IPM | Efficacy | Safety $LD_{50}$ (mg/kg) |
|---|---|---|---|---|---|
| 14 Dogs | 1-100 mg/kg/d; iv daily x 3 days | 22.5-2130 | 100 mg/kg/day x 3 days ($C_{max}$25-78 mcg/ml) | Not Tested | 1-5 mg/kg/day x 3 days (100% survival) |

TABLE 16

Intravenous IPM Lysine Salt

| # and Specie | Dose, Regimen and Duration | Total Dose of IPM (mg) | Plasma IPM | Efficacy | Safety $LD_{50}$ (mg/kg) |
|---|---|---|---|---|---|
| 80 Mice | 50-600 mg/kg/d; iv daily x 3 days | 4.3-80 | Not Tested | Not Tested | 220 |

The IPM MTD for dogs was 5 mg/kg/day×3 days and a correspondence starting dose in humans of 100 mg/m² per day for three (3) days should be a safe starting point. For IPM.(LYS)$_2$, the $LD_{10}$ for the intravenous three (3) day dose schedule in the mouse was calculated to be—133 mg/kg/day×3 days. IPM.(LYS)$_2$ is considered to be a minimally toxic alkylating agent with a steep therapeutic range. On mg/kg basis, the mean toxic dose (MTD) in humans for the lysine salt is estimated as ⅒ the $LD_{10}$ in mice or 40 mg/m²/d.

Estimated comparable human IV dosages are recorded in Table 17.

TABLE 17

Estimated Comparable Human Intravenous Dosages

| Drug | Species | Sub-acute IV $LD_{10}$ | Comparable Human IV Dosage |
|---|---|---|---|
| IPM | Mouse | 119 mg/kg/d | 30 mg/m²/d |
| IPM | Dog | 5 mg/kg/d | 100 mg/m²/d |
| IPM Lysine Salt | Mouse | 133 mg/kg/d | 40 mg/m²/d |

Example 8

This example describes the treatment of cancer in human subjects having metastatic ovarian cancer.

The subject is treated with IPM 500 mg/m² daily for three consecutive days via intravenous infusion. Her serum electrolytes, such as phosphorus and chloride are corrected with supplemental electrolytes, which are discontinued after seven days. BUN and creatinine are monitored normal limits.

Example 9

This example describes the results of treating human subjects with IPM.(LYS)$_2$. To date four (4) patients with advanced cancer have been treated with IPM.(LYS)$_2$.

The initial dose of IPM lysine salt was 30 mg/m² was administrated intravenously daily for three (3) days. One patient (cohort) was treated per dose escalation every 21-28 days to allow for toxicity presentation. Doses were escalated by 40% if there were no serious toxic events. Four patients have been treated—one at each dosage—30, 42, 59 and 83 mg/m² via daily IV administration for 3 days without serious toxicity. One patient with rectal cancer had stabilization of his disease following administration of 83 mg/m² of IPM.(LYS)$_2$ via daily IV administration for 3 days.

Example 10

This example describes the treatment of cancer non-small cell lung cancer which has progressed to metastatic infiltrating moderately differentiated adenocarcinoma. The status of the disease can be confirmed by CAT scan.

Isophosphoramide mustard lysine salt is administered at 350 mg/m² daily for three consecutive days intravenously. After a 21-day rest period, the three-day treatment protocol is repeated once. Daily blood fluid chemistry and hematological studies are monitored during treatments. The status of the cancer is monitored by CAT scan.

Example 11

This example demonstrates the effect of formation of an amine salt on compound stability.

Samples of lyophilized isophosphoramide mustard and its lysine salt were stored under varying conditions and assayed for purity. Results are presented in the table below:

| Compound | 0 months | 1 months | 3 months | 1 year |
|---|---|---|---|---|
| IPM, –23° C. | 97% | 88% | 70% | |
| IPM-LYS, –23° C. | 98% | | 98% | 100% |
| IPM-LYS, ambient | 98% | 98% | 65% | |

The invention claimed is:
1. A compound of the formula:

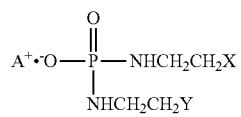

wherein A⁺ represents an ammonium species selected from the group consisting of quaternary ammonium, the conjugate acid of a basic amino acid, acyclic aliphatic ammonium, dialkyl ammonium, trialkyl ammonium, heterocyclic ammonium, aromatic ammonium, substituted and unsubstituted pyridinium, guanidinium, and amidinium; and X and Y independently represent leaving groups.

2. A compound of claim 1, wherein A⁺ represents BH⁺ and B is an amine selected from the group consisting of the basic amino acids, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tertbutylamine, tris(hydroxymethyl)methylamine, N,N-dimethyl-N-(2-hydroxyethyl)amine, tri-(2-hydroxyethyl)amine and N-methyl-D-glucamine.

3. A compound of claim 2, wherein the compound has the formula

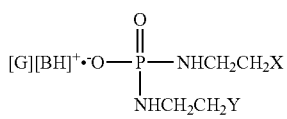

and G represents a second ammonium or amine species.

4. A compound of claim 2, wherein B is selected from the group consisting of lysine, homolysine, arginine, homoarginine, histidine, ornithine and combinations thereof.

5. A compound of claim 2, wherein B is lysine.

6. A compound of claim 2, wherein X and Y independently are selected from the group consisting of the halogens and the sulfonates.

7. A compound of claim 2, wherein X and Y are halogen.

8. A compound of claim 2, wherein X and Y are chlorine.

9. A compound of claim 3, wherein B and G are lysine and X and Y represent chlorine.

10. A salt comprising an isophosphoramide mustard anion and an ammonium cation, wherein the ammonium cation is selected from the group consisting of quaternary ammonium, the conjugate acid of a basic amino acid, acyclic aliphatic ammonium, dialkyl ammonium, trialkyl ammonium, heterocyclic ammonium, aromatic ammonium, substituted and unsubstituted pyridinium, guanidinium, and amidinium.

11. A salt of claim 10 further comprising a second amine or ammonium cation.

12. A salt of claim 10, wherein the ammonium cation is the conjugate acid of lysine or tris(hydroxymethyl)methylamine.

13. A pharmaceutical composition comprising a compound of claim 1 and a pharmaceutically acceptable carrier.

14. A pharmaceutical composition of claim 13, wherein X and Y independently are selected from the group consisting of the halogens and the sulfonates.

15. A pharmaceutical composition comprising a compound of claim 2 and a pharmaceutically acceptable carrier.

16. A pharmaceutical composition of claim 13, wherein X and Y are halogen.

17. A pharmaceutical composition of claim 13, wherein X and Y are chlorine.

18. A pharmaceutical composition of claim 13, wherein the composition comprises a solution formulated for administration to a human subject.

19. A pharmaceutical composition of claim 18, wherein the solution comprises from about 0.1 mg/mL to about 250 mg/mL of the compound.

20. A pharmaceutical composition of claim 19, wherein the solution comprises from about 20 to about 100 mg/mL of the compound.

21. A pharmaceutical composition of claim 13, wherein the composition comprises from about 200 mg to about 1500 mg of the compound per dosage unit.

22. A pharmaceutical composition comprising a compound of claim 3 and a pharmaceutically acceptable carrier.

23. A pharmaceutical composition comprising a compound of claim 9 and a pharmaceutically acceptable carrier.

24. A pharmaceutical composition comprising a salt of isophosphoramide mustard and an amine base; and a pharmaceutically acceptable carrier, wherein the amine base is selected from the group consisting of ammonia, a basic amino acid, acyclic aliphatic amine, dialkyl ammonium, trialkyl ammonium, heterocyclic amine, aromatic amine, substituted and unsubstituted pyridine, guanidine, and amidine.

25. A pharmaceutical composition of claim 24, wherein the composition comprises at least two equivalents of the amine base per equivalent of isophosphoramide mustard.

26. A pharmaceutical composition of claim 24, wherein the amine base is selected from the group consisting of basic amino acids, acyclic aliphatic amines, di- and tri-cyclicalkyl amines, heterocyclic amines, aromatic amines, substituted and unsubstituted pyridines, guanidines, and amidines.

27. A pharmaceutical composition of claim 24, wherein the amine base is selected from the group consisting of lysine, homolysine, arginine, homoarginine, histidine, ornithine and combinations thereof.

28. A composition according to claim 24, wherein the amine base is lysine or tris(hydroxymethyl)methylamine.

29. A lyophilisate comprising a compound of claim 1, produced by a method comprising contacting a compound of the formula

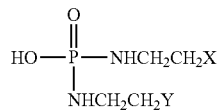

with at least one equivalent of an amine base selected from the group consisting of the basic amino acids, acyclic aliphatic amines, dialkyl ammonium, trialkyl ammonium, heterocyclic amines, aromatic amines, substituted and unsubstituted pyridines, guanidines, and amidines; in the presence of water; and lyophilizing the resulting mixture, thereby forming the lyophilisate.

30. A lyophilisate of claim 29, wherein X and Y are chlorine.

31. A lyophilisate of claim 29, wherein the lyophilisate is formed with at least two equivalents of the amine base.

32. A lyophilisate of claim 29, wherein the amine base is lysine or tris(hydroxymethyl)methylamine.

33. A compound of claim 2, wherein the compound is an anti-hyperproliferative compound.

34. A compound of claim 2, wherein the compound is more effective against CPA-resistant tumor growth than CPA, Ifos, or both.

35. A compound of claim 2, wherein B is tris(hydroxymethyl)methylamine.

36. A compound of claim 35, wherein X and Y are halogen.

37. A compound of claim 36, wherein X and Y are chlorine.

38. A pharmaceutical composition comprising the compound of claim 35 and a pharmaceutically acceptable carrier.

39. A pharmaceutical composition of claim 38, wherein the composition comprises a solution formulated for administration to a human subject.

40. A pharmaceutical composition of claim 15, wherein B is selected from the group consisting of lysine, homo lysine, arginine, homoarginine, histidine, ornithine and combinations thereof.

41. A pharmaceutical composition of claim 38, wherein the compound is a lyophilisate.

42. A compound of claim 13, wherein the compound is a lyophilisate.

43. A sterile aqueous solution suitable for administration to a human patient, comprising a compound dissolved directly therein of the formula:

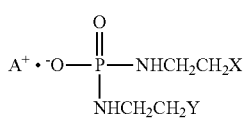

wherein A⁺ represents an ammonium species selected from the group consisting of quaternary ammonium, the conjugate acid of a basic amino acid, acyclic aliphatic ammonium, dialkyl ammonium, trialkyl ammonium, heterocyclic ammonium, aromatic ammonium, substituted and unsubstituted pyridinium, guanidinium, and amidinium; and X and Y independently represent leaving groups.

44. A sterile aqueous solution suitable for administration to a human patient, having dissolved directly therein
(i). a compound of the formula:

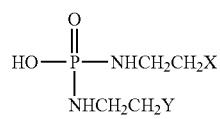

wherein X and Y independently represent leaving groups, and
(ii). an ammonium species selected from the group consisting of quaternary ammonium, the conjugate acid of a basic amino acid, acyclic aliphatic ammonium, dialkyl ammonium, trialkyl ammonium, heterocyclic ammonium, aromatic ammonium, substituted and unsubstituted pyridinium, guanidinium, and amidinium;
wherein the compound in the solution has a half-life at room temperature that is equal or greater to five times the half-life of the compound in solution in the absence of the ammonium species.

45. A sterile lyophilisate of a compound of the formula:

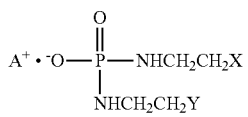

wherein A⁺ represents an ammonium species selected from the group consisting of quaternary ammonium, the conjugate acid of a basic amino acid, acyclic aliphatic ammonium, dialkyl ammonium, trialkyl ammonium, heterocyclic ammonium, aromatic ammonium, substituted and unsubstituted pyridinium, guanidinium, and amidinium; and X and Y independently represent leaving groups,
and wherein the lyophilisate is formed from a sterile solution of the compound dissolved in water.

46. The lyophilisate of claim 45, wherein A⁺ represents an acyclic aliphatic ammonium that includes one or more substitutions with a hydroxyl group; and X and Y independently are selected from the halogens and the sulfonates.

47. A lyophilisate of claim 46, wherein the acyclic aliphatic ammonium is selected from the group consisting of basic amino acids, mono-(2-hydroxyethyl)amine, bis-(2-hydroxyethyl)amine, tris-(2-hydroxyethyl)amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine.

48. A lyophilisate of claim 46, wherein the acyclic aliphatic ammonium is tris(hydroxymethyl)methylammonium, and X and Y are each chlorine.

49. A lyophilisate of claim 29, wherein the compound in the lyophilisate does not substantially undergo decomposition during storage of the lyophilisate for ten (10) months at −20° C.

\* \* \* \* \*